US008238623B2

(12) United States Patent
Stephan et al.

(10) Patent No.: US 8,238,623 B2
(45) Date of Patent: Aug. 7, 2012

(54) METHOD AND APPARATUS FOR CHARACTERIZING THE IMPERFECTIONS OF SKIN AND METHOD OF ASSESSING THE ANTI-AGING EFFECT OF A COSMETIC PRODUCT

(75) Inventors: Sandrine Stephan, Beaugency (FR); Michèle Neveu, Orleans (FR); Sylvianne Schnebert, Olivet (FR); Delphine Pelle De Queral, Ingre (FR)

(73) Assignee: LVMH Recherche, Saint Jean de Braye (FR)

( * ) Notice: Subject to any disclaimer, the term of this patent is extended or adjusted under 35 U.S.C. 154(b) by 927 days.

(21) Appl. No.: 11/543,587

(22) Filed: Oct. 4, 2006

(65) Prior Publication Data
US 2007/0086651 A1    Apr. 19, 2007

(30) Foreign Application Priority Data

Oct. 4, 2005    (FR) ...................................... 05 10146

(51) Int. Cl.
*G06K 9/00*    (2006.01)
*G06F 19/00*    (2011.01)
*A61B 5/00*    (2006.01)

(52) U.S. Cl. ........ 382/128; 382/100; 382/190; 382/224; 382/160; 702/179; 702/180; 702/181; 702/183; 424/9.8; 424/9.6; 424/69

(58) Field of Classification Search .................. 382/162, 382/100, 108, 190–195, 224, 282, 286, 159–160, 382/118, 128; 702/179–183; 424/9.8, 9.6, 424/69

See application file for complete search history.

(56) References Cited

U.S. PATENT DOCUMENTS 5,679,532 A * 10/1997 Repine ............................ 435/7.1
5,836,872 A * 11/1998 Kenet et al. .................... 600/306
(Continued)

FOREIGN PATENT DOCUMENTS
EP    1 314 395 A2    5/2003
(Continued)

*Primary Examiner* — Jingge Wu
*Assistant Examiner* — Avinash J Yentrapati
(74) *Attorney, Agent, or Firm* — Merchant & Gould P.C.

(57) ABSTRACT

The invention relates to a method and apparatus for characterizing the imperfections of the skin.
The apparatus comprises:
  a) a digital camera allowing the taking of at least one digital image of at least one determined skin zone, the said image being defined by a multiplicity of pixels, that is transmitted to a digital image processing device;
  b) means of splitting the digital image into three color planes: red, green, blue, termed R, G, B, with the aid of the said image processing device;
  c) means of extracting a single of these planes;
  d) means of calculating at least one of the following parameters on the basis of this plane:
    the mean grey level of the image;
    the surface area of the imperfections of the skin of the said image, some of which are related to aging, such as wrinkles, lines, spots, dark circles, pigmentary imperfections, slackening or loosening zones;
    the variance of the grey levels over the set of pixels of the image as parameter representative of the homogeneity of the skin.

The invention finds an industrial application in a method of assessing the anti-aging effect of a cosmetic product.

29 Claims, 2 Drawing Sheets

U.S. PATENT DOCUMENTS

| | | | |
|---|---|---|---|
| 6,081,612 A * | 6/2000 | Gutkowicz-Krusin et al. | 382/128 |
| 6,208,749 B1 * | 3/2001 | Gutkowicz-Krusin et al. | 382/128 |
| 6,547,729 B1 * | 4/2003 | Abbo | 600/300 |
| 6,551,982 B1 | 4/2003 | Ricci et al. | |
| 6,790,179 B2 * | 9/2004 | Skover | 600/306 |
| 6,811,536 B2 * | 11/2004 | Sun et al. | 600/500 |
| 6,916,288 B2 * | 7/2005 | Nakata | 600/306 |
| 7,071,167 B2 * | 7/2006 | Renault | 514/18.8 |
| 7,233,693 B2 * | 6/2007 | Momma | 382/162 |
| 7,454,046 B2 * | 11/2008 | Chhibber et al. | 382/128 |
| 7,556,605 B2 * | 7/2009 | Qu et al. | 600/587 |
| 2002/0016539 A1 * | 2/2002 | Michaelis et al. | 600/407 |
| 2003/0003509 A1 * | 1/2003 | Uchida | 435/7.1 |
| 2003/0063801 A1 * | 4/2003 | Rubinstenn et al. | 382/190 |
| 2003/0065256 A1 * | 4/2003 | Rubinstenn | 600/407 |
| 2003/0087333 A1 * | 5/2003 | Hirai et al. | 435/40.5 |
| 2003/0099383 A1 * | 5/2003 | Lefebvre | 382/128 |
| 2003/0223622 A1 * | 12/2003 | Simon et al. | 382/118 |
| 2004/0120918 A1 * | 6/2004 | Lintner et al. | 424/70.14 |
| 2004/0122299 A1 * | 6/2004 | Nakata | 600/306 |
| 2004/0146474 A1 * | 7/2004 | Galey | 424/70.13 |
| 2004/0147443 A1 * | 7/2004 | Renault | 514/12 |
| 2004/0166178 A1 * | 8/2004 | Meybeck et al. | 424/725 |
| 2004/0170337 A1 * | 9/2004 | Simon et al. | 382/254 |
| 2004/0218810 A1 * | 11/2004 | Momma | 382/162 |
| 2004/0260178 A1 * | 12/2004 | Kahn et al. | 600/437 |
| 2005/0196461 A1 * | 9/2005 | Udell | 424/549 |
| 2005/0203355 A1 * | 9/2005 | Stamatas et al. | 600/317 |
| 2005/0261367 A1 * | 11/2005 | Murad | 514/492 |
| 2006/0052719 A1 * | 3/2006 | Ruvolo et al. | 600/552 |
| 2007/0010430 A1 * | 1/2007 | Sato et al. | 514/8 |
| 2007/0040907 A1 * | 2/2007 | Kern et al. | 348/77 |
| 2007/0058858 A1 * | 3/2007 | Harville et al. | 382/165 |
| 2007/0064985 A1 * | 3/2007 | Chhibber et al. | 382/128 |
| 2007/0086651 A1 * | 4/2007 | Stephan et al. | 382/162 |
| 2008/0045467 A1 * | 2/2008 | Kim et al. | 514/26 |
| 2008/0212894 A1 * | 9/2008 | Demirli et al. | 382/276 |
| 2009/0053695 A1 * | 2/2009 | Tanigawara et al. | 435/6 |
| 2009/0141956 A1 * | 6/2009 | Chhibber et al. | 382/128 |

FOREIGN PATENT DOCUMENTS

| | | |
|---|---|---|
| EP | 1314395 A2 * | 5/2003 |
| EP | 1 512 372 A1 | 3/2005 |
| EP | 1 523 936 A1 | 4/2005 |
| WO | WO 00/67398 | 11/2000 |

* cited by examiner

METHOD AND APPARATUS FOR CHARACTERIZING THE IMPERFECTIONS OF SKIN AND METHOD OF ASSESSING THE ANTI-AGING EFFECT OF A COSMETIC PRODUCT

The invention relates to a method and apparatus for characterizing the imperfections of the skin and its application in a method of assessing the anti-aging effect of a cosmetic product.

PRIOR ART

The document U.S. Pat. No. 6,551,982 B1 discloses a procedure and a device for the noninvasive estimation of a relative age of a person based on a procedure much like infrared termed NIR using a wavelength in the region from 700 to 2500 nanometers.

Further, the document WO 00/67398 A1 discloses imaging systems and procedures for analysing the skin implementing the acquisition and the creation of various digital images with the aim of viewing skin defects, and thereafter the consideration of a subimage containing the skin defect.

AIMS OF THE INVENTION

The present invention is aimed at solving the technical problem consisting of the provision of a novel method and of a novel apparatus for characterizing the imperfections of the skin that are relatively easy to implement, sure and reliable as regards the result obtained.

The present invention is further aimed at solving the technical problem consisting of the provision of a method of assessing the anti-aging effect of a cosmetic product implementing the method or the apparatus for characterizing the imperfections of the skin.

The present invention affords a satisfactory solution to these two technical problems.

DETAILED DESCRIPTION OF THE INVENTION

According to a first aspect, the present invention provides a method of characterizing the imperfections of the skin of a person, characterized in that it comprises the following steps:

a) taking at least one digital image of at least one determined skin zone, the said image being defined by a multiplicity of pixels, with the aid of a digital video camera or digital photo or picture camera, that is transmitted to a digital image processing device;

b) splitting the digital image into three colour planes: red, green, blue, termed R, G, B, with the aid of the said image processing device;

c) extracting a single of these planes;

d) calculating at least one of the following parameters, by appropriate means of calculation, on the basis of this plane:
  the mean grey level of the image;
  the surface area of the imperfections of the skin of the said image, some of which are related to aging, such as wrinkles, sign lines, spots, dark circles, pigmentary imperfections, slackening or loosening zones;
  the variance of the grey levels over the set of pixels of the image as parameter representative of the homogeneity of the skin.

According to a particular embodiment of this method, the latter is characterized in selecting a colour plane representative of the imperfection to be observed. By the terms "representative of the imperfection to be observed" qualifying a colour plane, it is meant a colour plane enabling to obtain visually the best showing of the imperfection to be observed. On the selected colour plane, it is carried out the aforesaid parametrization of at least one parameter chosen from among the mean grey level of the image, the surface area of the skin imperfections, some of which are related to aging and the variance. By way of example for the observation of wrinkles, lines and pigmentary defects or imperfections, it will usually be selected the plan of blue colour, although other colour planes could be selected as well.

According to another particular embodiment of the invention method, the taking of a digital image of at least one skin zone is performed under lightening with a white light or with an ultraviolet light. The selection of the lightening between the white light and the ultraviolet light is dictated by the nature of the imperfections to be observed. In particular, the lightening in ultraviolet light, produced for example with the help of a well-known Wood lamp, enables a good showing of the pigmentary spots and of the cutaneous photo-ageing.

According to an another particular embodiment of this method, the latter is further characterized in that a thresholding of the grey levels is carried out, that is to say the grey levels below a certain predetermined grey level threshold are eliminated, so as to eliminate the spurious elements.

According to yet another particular embodiment of this method, the latter is characterized in that a limited area of the skin of the person to be analysed is chosen, on which the analysis of the skin imperfections is undertaken on the entirety of this area.

According to a particular variant embodiment, the process is characterized in that the limited area of the skin represents a surface area of about 1 cm$^2$ to 10 cm$^2$.

According to an advantageous characteristic of the method on the invention, the latter is characterized in that an enlargement of the said image obtained by the video camera or the still photo or picture camera is performed allowing an operator to better view the skin imperfections and to evaluate the thresholding of the grey levels making it possible to eliminate the spurious elements or artefacts.

According to an advantageous embodiment of the method according to the invention, the latter is characterized in that a digital colour video camera of TRI-CCD type or a digital still photo or picture camera is used. Such a colour video camera is available commercially in particular from the company SONY; and such a digital still photo or picture camera, for instance of type D70S, is available commercially from the company NIKON.

According to a particular embodiment of the method on the invention, the latter is characterized in that at least one image or a plurality of images of the skin of one and the same person is or are recorded, in particular over several different zones, on a device for recording digital data.

According to a particular variant embodiment, said image-taking zone is corresponding to any cutaneous zone representative of the global ageing of the face or of the body. Advantageously, said zone will be selected from the group consisting of an outer zone of the eye (crow's-foot), of a middle zone of the brow; of a zone of the cheek and of a zone of the nasogenian furrow.

According to a second aspect, the present invention provides an apparatus for characterizing the imperfections of the skin of a person, characterized in that it comprises:

a) a digital video camera or a digital still photo or picture camera allowing the taking of at least one digital image of at least one determined skin zone, the said image being defined by a multiplicity of pixels, that is transmitted to a digital image processing device;

b) means of splitting the digital image into three colour planes: red, green, blue, termed R, G, B, with the aid of the said image processing device;

c) means of extracting a single of these planes;

d) means of calculating at least one of the following parameters on the basis of this plane:
- the mean grey level of the image;
- the surface area of the imperfections of the skin of the said image, some of which are related to aging, such as wrinkles, sign lines, spots, dark circles, pigmentary imperfections, slackening or loosening zones;
- the variance of the grey levels over the set of pixels of the image as parameter representative of the homogeneity of the skin.

According to a particular embodiment of this apparatus, the latter is characterized in that extraction means carry out the extraction of the colour plane representative of the imperfection to be observed, on which calculation means carry out the aforesaid calculation of at least one parameter chosen from among the mean grey level of the image, the surface area of the skin imperfections, some of which are related to aging, and the variance.

According to another particular embodiment of the invention apparatus, the latter further comprises a lightening device to lighten with a white light or with an ultraviolet light enabling the taking of at least one image of at least one skin zone under such a lightening, in particular, the lightening device lightening in ultraviolet light can be constituted by, or comprises, a Wood lamp.

According to an another particular embodiment of this apparatus, the latter is further characterized in that it comprises means of consideration of a thresholding of the grey levels, that is to say means making it possible to eliminate the grey levels below a certain predetermined grey level threshold, so as to eliminate the spurious elements.

According to yet another particular embodiment of this apparatus, the latter is characterized in that there is provision for taking the said image of a limited area of the skin of the person to be analysed, on which calculation means undertake the analysis of the skin imperfections over the entirety of this area.

According to an advantageous characteristic of the apparatus on the invention, the latter is characterized in that it comprises means of enlargement of the said image obtained by the digital video camera or the digital still picture or photo camera, allowing an operator to better view the skin imperfections and to evaluate the thresholding of the grey levels making it possible to eliminate the spurious elements or artefacts.

According to a particular variant embodiment, this apparatus is characterized in that it comprises means for extracting from an image of an area of the skin, taken by means of the said video camera or still photo or picture camera, a zone of interest exhibiting an area of about 1 $cm^2$ to 10 $cm^2$.

According to an advantageous embodiment of the apparatus according to the invention, the latter is characterized in that a digital colour video camera of TRI-CCD type, or a digital still photo or picture camera, is provided. Such a colour video camera is available commercially in particular from the company SONY; and such a digital still photo or picture camera, for example of type D70S, is available commercially from the company NIKON.

According to a particular embodiment of the apparatus according to the invention, the apparatus is characterized in that it comprises means of recording at least one image or a plurality of images of the skin of one and the same person, in particular over several different zones, on a device for recording digital data.

According to a further particular embodiment of the apparatus according to the invention, the apparatus is characterized in that it comprises a computer combined with a monitor comprising a screen, keyboard and mouse and comprising software integrating the whole of the aforesaid means including:
- the means of splitting the digital image into three colour planes: red, green, blue, termed R, G, B;
- the means of extracting a single of these planes, which plane is the most representative of the imperfection to be observed;
- the means of calculating at least one of the following parameters on the basis of this plane:
  - the mean grey level of the image;
  - the surface area of the imperfections of the skin of the said image, some of which are related to aging, such as wrinkles, sign lines, spots, pigmentary imperfections, slackening or loosening zones;
- the means of consideration of a thresholding of the grey levels;
- the means of enlargement of the said image;
- the means of recording at least one image or a plurality of images of the skin.

According to an advantageous mode of relation of the invention of the method and of the apparatus for characterizing the imperfections of the skin, the calculation means take into account the mean of each parameter obtained over the different images obtained respectively with the different zones of the face that are considered, so as to obtain each global mean parameter of the face which is advantageously recorded and can, according to a variant embodiment, be used, for each person, to constitute a calibration curve for the age of the skin.

According to a third aspect, the present invention relates further to a method of assessing the anti-aging effect of a cosmetic product, characterized in that the method of characterizing the imperfections of the skin is used on each person of a representative group of people, such as defined previously or such as results from the following description; and for each person:
- taking at least one first digital image before treatment with the said cosmetic product of at least one determined skin zone to determine the reference parameters of the skin before treatment;
- taking at least one second digital image after a predetermined time period of the said treatment with the cosmetic product and the same parameters are determined on the said second image;
- comparing the parameters of the second image of the same skin zone obtained after treatment with respect to the parameters of the first image of skin before treatment;
- determining the means of each parameter over the set of people of the group; and
- reaching a conclusion of the positive effectiveness of the anti-ageing effect of the cosmetic product considered when at least one of the mean parameters considered chosen from among the mean grey levels of the image, the area or else the imperfections and/or the variance of the grey levels has decreased significantly with respect to the mean of the parameters of the first image.

According to an advantageous embodiment of this method, the latter is characterized in that the significant decrease is obtained with a probability of error of less than or equal to 5%.

According to another advantageous embodiment of this method, the latter is characterized in that this anti-aging effect is carried out on a panel of people of a group representative of a given age category, so as to determine the significant character of anti-aging effectiveness of the cosmetic product considered.

According to yet another advantageous embodiment of this method, the latter is characterized in that the first image and the second image are recorded on each of the different characteristic zones of the ageing of the skin on the face and/or the body, in particular:
an outer zone of the eye (crow's-foot),
a middle zone of the brow;
a zone of the cheek, and
a zone of the nasogenian furrow.

By virtue of the methods and the apparatus according to the invention, the previously stated technical problems are solved in a simple, sure and reliable manner.

Other aims, characteristics and advantages of the invention will be clearly apparent in the light of the explanatory description which follows given with reference to a currently preferred embodiment of the invention.

EXAMPLE 1

Figure 1:
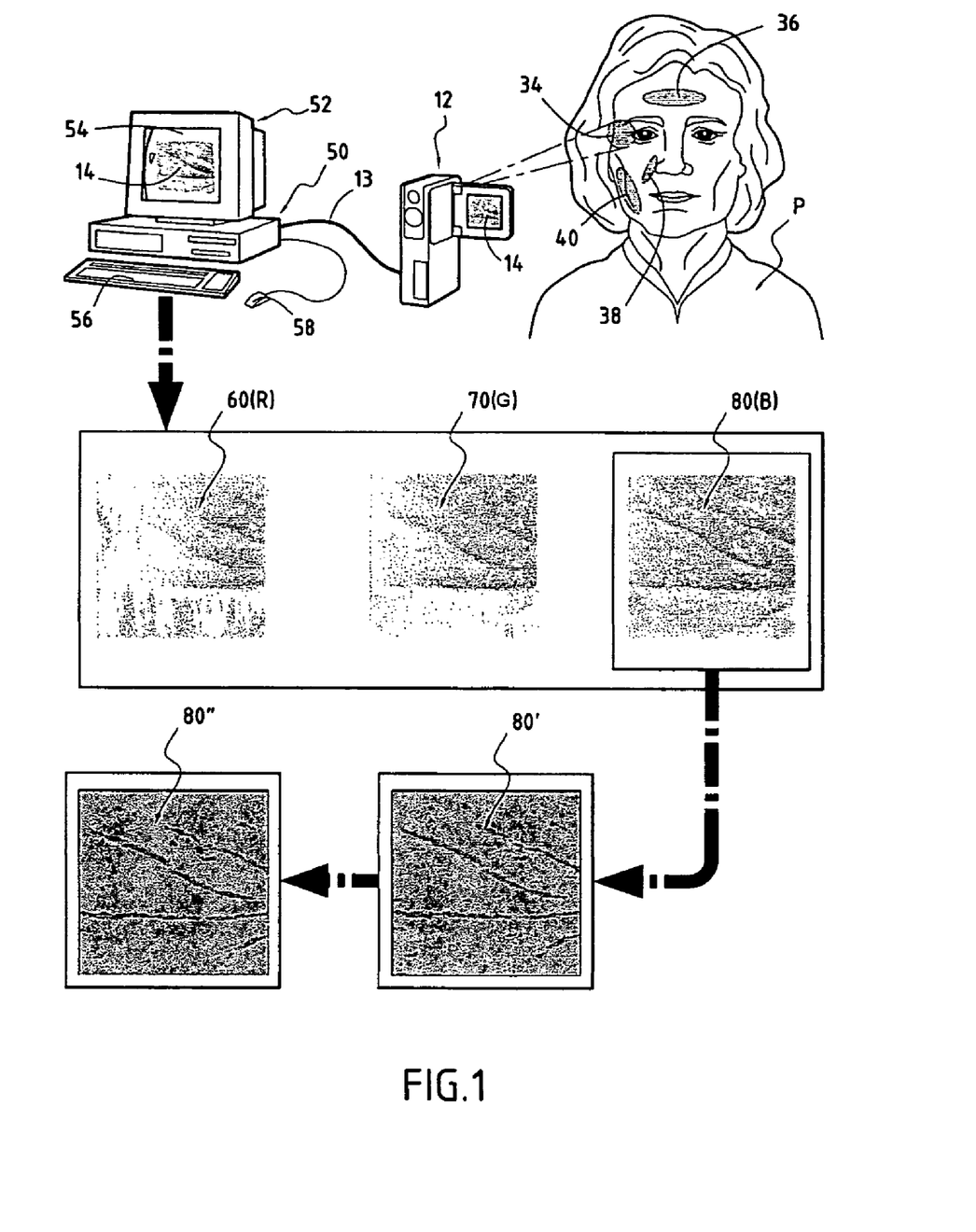
FIG. 1 represents an apparatus for characterizing the imperfections of the skin of a person, making it possible to implement the previously described method of characterizing the imperfections of the skin.

Description of the Apparatus Represented in FIG. 1

With reference to FIG. 1, there is represented a currently preferred embodiment of an appliance according to the invention, represented by the general reference numeral 10. To guarantee an accuracy of positioning of the person P, the latter will be seated on a repositioning table, for example available commercially under the brand name VISIOFACE, from the company EOTECH, France.

This apparatus 10 is designed to carry out the characterization of the imperfections of the skin of a person, and is characterized in that it comprises:
a) a digital video camera or digital still photo or picture camera 12 allowing the taking of at least one digital image 14, of at least one determined skin zone 34, 36, 38, 40, the said image being defined by a multiplicity of pixels, that is transmitted to a digital image processing device.

For the needs of these images taking, the determined skin zones are lightened by a lightening device, not shown here, lightening with a white light or with an ultraviolet light, depending from the nature of the imperfections to be observed.

According to an advantageous embodiment of the apparatus according to the invention, a digital colour video camera 12 of TRI-CCD type is provided, such a colour camera being available commercially in particular from the company SONY; or a digital still photo or picture camera of type D70S, available commercially from the company NIKON.

According to a particular variant embodiment, the said video camera 12 or still photo or picture camera makes it possible to take an image of an area of the skin having from 1 $cm^2$ to 10 $cm^2$.

Also, as is well known to the person skilled in the art, such a digital image processing device is available commercially for example in the form of software, such as the VISILOG 6.2 image analysis software, that it is possible to integrate with a computer 50 linked to the said camera 12 by an appropriate lead 13. The said computer 50 is naturally combined with a monitor 52 together with its screen 54 and its keyboard 56 and a mouse 58.

b) the digital image processing device comprises means of splitting the digital image into three colour planes: red 60, green 70, blue 80, termed R, G, B, c) the digital image processing device also comprises means of extracting a single of these planes; here preferably the plane termed blue 80, corresponding to the colour blue, d) means of calculation, here envisaged in the said software, of at least one of the following parameters on the basis of this plane:
the mean grey level of the image;
the surface area of the imperfections of the skin of the said image, some of which are related to aging, such as wrinkles, sign lines, spots, dark circles, pigmentary imperfections, slackening or loosening zones;
the variance of the grey levels over the set of pixels of the image as parameter representative of the homogeneity of the skin.

It will be noted that the blue plane 80 is often preferred since it presents the most contrast and allows better viewing of the most of the skin imperfections.

It is possible to apply, to the extracted blue plane 80, a mathematical filter envisaged in the image analysis software to eliminate spurious noise from the image such as reflection.

According to yet another particular embodiment of this apparatus, the latter is characterized in that provision is made for taking the said image of a limited area 34, 36, 38, 40, of the skin of the person P to be analysed, on which the calculation means undertake the analysis of the skin imperfections over the entirety of this area.

According to an advantageous characteristic of the apparatus on the invention, the apparatus comprises means of enlargement, for example an enlargement of four times so as to magnify the details, again integrated with the said software of the said image obtained by the camera allowing an operator to better view the skin imperfections and to evaluate the thresholding of the grey levels making it possible to eliminate the spurious elements or artefacts.

According to another advantageous characteristic of the apparatus according to the invention, the apparatus comprises means of consideration of a thresholding of the grey levels, again integrated with the software, that is to say means making it possible to eliminate the grey levels below a certain predetermined grey level threshold, so as to eliminate the spurious elements, thus producing an image 80' ridded of the spurious elements.

Also advantageously envisaged is a second mathematical filtering, also envisaged in the software, so as to eliminate the tiny zones detected during the preceding step of thresholding and presenting no interest, here obtaining an image 80" on which the skin imperfections are very clearly apparent. It is on the latter image 80" that the image analysis and calculation steps are preferably carried out.

Thus within the framework of the invention, these image analyses are carried out on the macro-photographs, in particular 80, 80' or preferably 80", of the middle zone of the brow 36, on the zone of the crow's-foot 34, on the zone of the nasogenian furrow 38 and on the middle zone of the cheek 40.

According to a particular embodiment of the apparatus according to the invention, the apparatus comprises means of recording, integrated with the software, of at least one image or a plurality of images of the skin of one and the same person, in particular over several different zones here four zones 34, 36, 38 and 40, on a device for recording digital data integrated with the software.

According to another particular embodiment of the apparatus according to the invention, the apparatus is characterized in that the means of calculation take into account the mean of each parameter obtained over the four images obtained respectively with the four zones of the face that are considered 34, 36, 38 and 40, so as to obtain each global mean parameter of the face which is advantageously recorded and can, according to a variant embodiment, be used, for each person, to constitute a calibration curve for the age of the skin.

Figure 3:
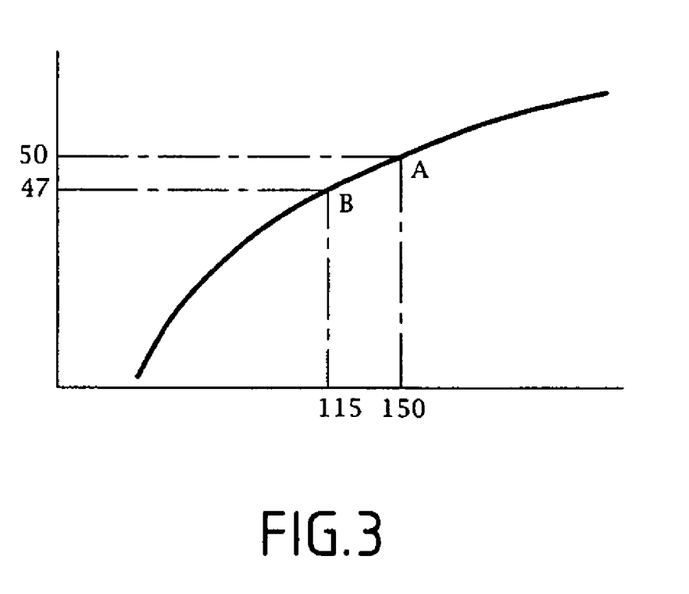
FIG. 3 represents a curve of the apparent age of the skin of a person before treatment (point A) and after treatment with a tested cosmetic product (point B).

By virtue of the apparatus according to the invention, it is possible to implement the establishment of a calibration curve for real age as indicated in example 2, which makes it possible to determine the apparent age of a person as shown in FIG. 3.

EXAMPLE 2

Establishment of a Calibration Curve Matching Real Age with One of the Three Parameters for Characterizing the Imperfections of the Skin Chosen from Among the Mean Grey Level of the Image, the Surface Area of the Imperfections of the Skin, and/or the Variance of the Grey Levels Over the Set of Pixels of the Image For this purpose, a sample of women statistically representative of the age category ranging from 20 to 55 years, made up of 70 people, is selected.

For each person, the variance of the grey levels over the set of pixels of the image obtained on the four zones of the skin of each person, constituted by the outer zone of the eye (or crow's-foot), the middle zone of the brow; the zone of the cheek and the zone of the nasogenian furrow is determined with the aid of the previously defined method of characterizing the imperfections of the skin.

Figure 2:
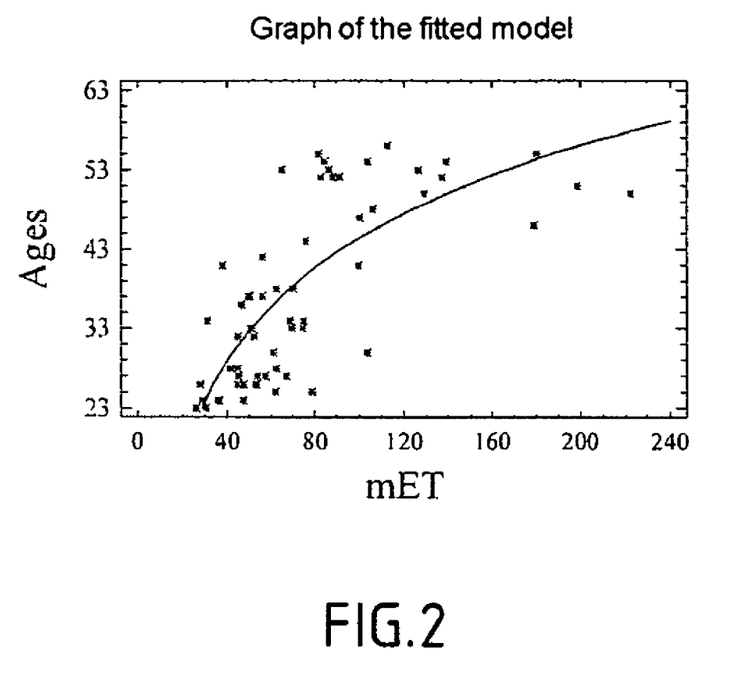
FIG. 2 represents a calibration curve of apparent age obtained with a sample of a group of 70 women aged between 23 and 54 years.

The mean variance obtained over these four zones for each person is scored and charted on an orthonormal curve whose abscissa consists of the mean of the variance of the grey levels over the four skin zones (value M), and as ordinate the real age of the people of the group stretching from 23 years to 55 years, charting the entirety of the measurements obtained over the mean variances for the entirety of the women. The curve represented in FIG. 2 is obtained, which is defined by the equation Ages=$-33+16.9 \times \ln$ (M).

ln=Naperian log in this equation.

EXAMPLE 3

Test for Evaluating the Effectiveness of a Cosmetic Product

Within the framework of this example according to the invention, the effectiveness is determined of a cosmetic product of the following composition, as a percentage by weight:

Extract of mallow . . . 3% (for this product the extract of mallow is the product Vitactyl® marketed by the company SILAB, Brives, France).

| | |
|---|---|
| Extract of tormentil | 0.5% |
| Extract of beech bud | 2% (product Gatuline ® RC) |
| Aqueous alcoholic solution of extract of *Longosa* containing 0.5% by dry weight of extract of *Longosa* | 2% |
| Magnesium gluconate | 0.05% |
| Emulsified excipients in the form of oil in water QSP | 100% |

To carry out this trial, a panel is made up from 30 women volunteers of an age category lying between 44 and 64 years, with a mean at 54 years.

For each of the women of this group of 30 people, the procedure for assessing the anti-aging effect of this cosmetic product is implemented, that is to say, for each person:

a) taking of at least one first digital image before treatment of the said cosmetic product of at least one zone of the determined skin, here in practice of four zones of the determined skin, namely: a middle zone of the brow, a zone of the cheek, an outer zone of the eye (crow's-foot) and a zone of the nasogenian furrow.

Thereafter, the mean of the data measured on each person is determined for each parameter comprising in particular the mean grey level of the image, the surface area of the imperfections of the skin of the said first image, some of which are related to aging, such as wrinkles, sign lines, pigmentary defects, spots; the variance of the grey levels over the set of pixels of the image as parameter representative of the homogeneity of the skin.

The means of the data measured before treatment are reported in table I.

The application of the cosmetic product is undertaken twice a day, in the morning on rising and in the evening on retiring, for four weeks.

Thereafter at least one second image is taken on which are carried out the same measurements and determinations of the same parameters relating to the area and the variance which are also charted in table I with the label, "one month", that is to say a month after the start of the treatment.

It will be noted that it would have been quite possible to choose the mean grey level of the image as one of the parameters charted in the table.

The appliance used and the TRI-CCD camera, combined with the Visilog version 6.2 software described within the framework of the appliance of example 1.

On the basis of table I, it is observed that under the conditions of the study, the cosmetic product tested significantly improves the homogeneity of the skin. Specifically, one finds a decrease in the area of the objects detected on each zone of the face and significant decrease in the mean variance over the four tested zones of the face.

TABLE I

| | MEAN OF THE MEASURED DATA | | | |
|---|---|---|---|---|
| | before | 1 month | p* | percentage |
| BROW | | | | |
| area | 24987.5 | 20801.1 | S (=0.02) | −17% |
| variance | 109.4 | 103.3 | NS | |

TABLE I-continued

MEAN OF THE MEASURED DATA

|  | before | 1 month | p* | percentage |
|---|---|---|---|---|
| EYE |  |  |  |  |
| area | 13604.4 | 09786.2 | S (<0.01) | −28% |
| variance | 133.5 | 105.7 | S (=0.04) | −21% |
| FURROW |  |  |  |  |
| area | 12092.0 | 10546.0 | S (<0.01) | −13% |
| variance | 90.1 | 79.7 | S (=0.02) | −12% |
| CHEEK |  |  |  |  |
| area | 29830.7 | 22952.2 | S (<0.01) | −23% |
| variance | 48.1 | 38.6 | S (<0.01) | −20% |
| B + C + E + F |  |  |  |  |
| variance | 95.3 | 81.8 | S (<0.01) | −14% |

Represented in FIG. 3 is a curve of the type of that obtained in FIG. 2 for a given woman having a real age of 52 years.

On the basis of the first image, its mean variance has been measured over the aforesaid four skin zones considered and the point A has been obtained which gives her an apparent age of her skin of 50 years.

After treatment with the cosmetic product considered in this example, the variance obtained gives the point B with an apparent age of 47 years after treatment.

It is found that this curve constitutes in practice an index for measuring the anti-aging effect of the cosmetic product which constitutes for the cosmetician a "youth index" that can be supplemented with the opinion of an expert and the opinion of the woman herself on the effectiveness of the product on her skin.

The invention also covers all the means constituting technical equivalents of the means described as well as diverse combinations.

The invention claimed is:

1. A method of characterizing wrinkles, sign lines, slackening and/or loosening of the skin of the face of a person, comprising the following steps:
   a) taking at least one digital image of at least one predetermined skin face surface area where said wrinkles, sign lines, slackening and/or loosening of the skin occur, selected from an outer zone of the eye or crow's-foot, and a skin zone of the nasogenian furrow; said image being defined by a multiplicity of pixels with the aid of a digital video camera or a digital picture camera, that is transmitted to a digital image processing device;
   b) splitting the recorded digital image into three colour planes: red, green, blue, termed R, G, B, with the aid of said image processing device;
   c) extracting a single of these planes;
   d) calculating, by appropriate means of calculation, on the basis of this extracted plane, at least the variance of the grey levels over the set of pixels of the image as parameter representative of the homogeneity of the skin, and optionally at least one of the following parameters:
      i) the mean grey level of the image;
      ii) the surface area of the outer zone of the eye and skin zone of the nasogenian furrow of the said image;
   e) recording on a device for recording digital data, the calculated variance of the grey level as a parameter characterizing the wrinkles, sign lines, slackening and/or loosening of the skin of the face; and
   f) preparing a calibration curve of age versus the variance of the grey levels for a representative group of persons; thereby characterizing said wrinkles, sign lines, slackening and/or loosening of the skin of the face,
   wherein the calibration curve takes into account the mean of at least the variance obtained from a plurality of images from a plurality of ageing zones of the face from a plurality of individuals.

2. The method of claim 1, wherein said extraction step comprises selecting a colour plane representative of the ageing to be observed and performing, on the selected colour plane, said calculating of said at least one parameter selected from the mean grey level of the image, the surface area of the ageing zones of the skin, and the variance of the grey levels.

3. The method of claim 1, comprising selecting the plane of blue colour.

4. The method of claim 1, comprising performing the taking of said image of at least one zone of the face skin under a lightening selected from a lightening with white light and a lightening with ultraviolet light.

5. The method of claim 1, comprising a thresholding of the grey levels, for eliminating the grey levels below a predetermined grey level threshold, thereby eliminating spurious elements or artefacts.

6. The method of claim 1, wherein said limited surface area represents a surface area of about 1 $cm^2$ to 10 $cm^2$.

7. The method of claim 1, comprising performing an enlargement of said image obtained by said video camera or said picture camera, thereby allowing an operator to better view the skin imperfections and evaluating the thresholding of the grey levels to eliminate the spurious elements or artefacts.

8. The method of claim 1, comprising said digital camera is selected from a TRI-CCD digital colour video camera and a D70S digital picture camera of type.

9. The method of claim 1, comprising recording at least one image or a plurality of images of the skin of one and the same person on said device for recording digital data.

10. The method of claim 1, comprising selecting in said skin face area, in addition to the outer zone of the eye or crow's-foot, and the zone of the nasogenian furrow, at least one of a middle zone of the brow; and of a zone of the cheek.

11. The method of claim 10, comprising taking four images obtained respectively with the outer zone of the eye or crow's-foot, the middle zone of the brow; the zone of the cheek, the zone of the nasogenian furrow face; and the calculation means take into account the mean of each parameter obtained over the four images obtained respectively with the four zones of the face; thereby obtaining each global mean parameter of the face which is recorded and may be used, for each person, to constitute a calibration curve for the age of the skin.

12. A method of assessing the anti-aging effect of a cosmetic product, comprising implementing the method of claim 1, on each person of a representative group of persons; and for each person:
   taking at least one first digital image before treatment with said cosmetic product of at least one predetermined skin face surface area where wrinkles, sign lines, slackening and/or loosening of the skin occur, selected from an outer zone of the eye or crow's-foot, and a skin zone of the nasogenian furrow; and determining the reference parameters of the skin before treatment;
   taking at least one second image after a predetermined time period of said treatment with the cosmetic product and determining the same parameters on said second image;
   the parameters of the second image of the same skin zone obtained after treatment are compared with respect to the parameters of the first image of skin before treatment;

the means of each parameter are determined over the set of people of the group; and reaching a conclusion of positive effectiveness of the anti-wrinkle effect of the cosmetic product considered when at least the variance of the grey levels, and optionally at least one of the mean parameters considered chosen from the group comprising the mean grey levels of the image, the surface area of the ageing zones, has decreased significantly with respect to the mean of the parameters of the first image.

13. The method of claim 12, wherein the significant decrease is obtained with a probability of error of less than or equal to 5%.

14. The method of claim 12, comprising assessing this anti-aging effect on a panel of people of a group representative of a given age category, so as to determine the significant anti-aging effectiveness of the cosmetic product considered.

15. The method of claim 12, comprising recording the first image and the second image on each of the different zones characterizing the aging of the skin face.

16. The method of claim 12, wherein the different surface areas of the skin are selected from:
   i) the outer zone of the eye (crow's-foot),
   ii) the middle zone of the brow;
   iii) the zone of the cheek,
   iv) the zone of the nasogenian furrow, and
   v) a plurality or all of said zones.

17. An apparatus for characterizing wrinkles, sign lines, slackening and/or loosening of the skin of the face of a person, comprising:
   a) a digital video camera or a digital picture camera allowing the taking of at least one digital image of at least one predetermined face skin surface area where said wrinkles, sign lines, slackening and/or loosening of the skin occur, selected from an outer zone of the eye or crow's-foot, and a skin zone of the nasogenian furrow; said image being defined by a multiplicity of pixels transmitted to a digital image processing device;
   b) means for splitting the digital image into three colour planes: red, green, blue, termed R, G, B, with said image processing device;
   c) means of extracting a single of these planes;
   d) means of calculating, by appropriate means of calculation, on the basis of this extracted plane, at least the variance of the grey levels over the set of pixels of the image as parameter representative of the homogeneity of the skin, and optionally at least one of the following parameters:
      i) the mean grey level of the image;
      ii) the surface area of the outer zone of the eye and skin zone of the nasogenian furrow of the said image;
   e) a device for recording digital data for recording the calculated variance of the grey level as a parameter characterizing the wrinkles, sign lines, slackening and/or loosening of the skin of the face; and
   f) said means of calculation preparing a calibration curve of age versus the variance of the grey levels for a representative group of persons;
   thereby characterizing said wrinkles, sign lines, slackening and/or loosening of the skin of the face,
   wherein the calibration curve takes into account the mean of at least the variance obtained from a plurality of images from a plurality of ageing zones of the face from a plurality of individuals.

18. The apparatus of claim 17, wherein the extraction means carry out the extraction of a colour plane representative of the skin face ageing to be observed.

19. The apparatus of claim 17, comprising a lightening device for lightening in white light or in ultraviolet light allowing taking of at least one image of at least zone of the face skin under such a lightening.

20. The apparatus of claim 17, comprising means for thresholding of the grey levels, for eliminating the grey levels below a predetermined grey level threshold, thereby eliminating the spurious elements or artefacts.

21. The apparatus of claim 17, wherein said surface area of the skin represents a surface area of about 1 $cm^2$ to 10 $cm^2$.

22. The apparatus of claim 17, wherein comprising means of enlargement of said image obtained by the camera for allowing an operator to better view the skin imperfections and evaluating thresholding of the grey levels thereby eliminating the spurious elements or artefacts.

23. The apparatus of claim 17, comprising means of recording at least one image or a plurality of images of the skin of one and the same person, or each person of a group of persons, on said device for recording digital data.

24. The apparatus of claim 17, wherein the surface areas are selected from:
   i) the outer zone of the eye (crow's-foot),
   ii) the middle zone of the brow;
   iii) the zone of the cheek,
   iv) the zone of the nasogenian furrow, and
   v) a plurality or all of said zones.

25. The apparatus of claim 17, comprising a computer combined with a monitor comprising a screen a keyboard and a mouse and comprising a software integrating said means including:
   a) the means of splitting the digital image into three colour planes: red, green, blue, termed R, G, B;
   b) the means of extracting a single of these planes;
   c) means of calculating, by appropriate means of calculation, on the basis of this extracted plane, at least the variance of the grey levels over the set of pixels of the image as parameter representative of the homogeneity of the skin, and optionally at least one of the following parameters:
      i) the mean grey level of the image;
      ii) the surface area of the outer zone of the eye and skin zone of the nasogenian furrow of the said image;
   d) means of consideration of a thresholding of the grey levels;
   e) means of enlargement of the said image; and
   f) means of recording at least one image or a plurality of images of the skin.

26. The apparatus of claim 17, wherein the calculation means take into account the mean of each parameter obtained over four images obtained respectively with the four ageing zones of the face that are considered, so as to obtain each global mean parameter of the face which is advantageously recorded and can, according to a variant embodiment, be used, for each person, to constitute said calibration curve for the age of the skin.

27. The apparatus of claim 17, comprising extracting the plane termed blue corresponding to the colour blue.

28. A method of assessing the anti-aging effect of a cosmetic product, comprising
   a) taking a pre-application digital image of a plurality of control subjects prior to use of the cosmetic product of at least one of the following skin zones of surface area where the skin ageing occurs: middle zone of the brow, a zone of the cheek, an outer zone of the eye, and a zone of the nasogenian furrow;
   b) measuring the variance of the grey levels over the set of pixels of the pre-application image;

c) preparing a calibration curve of age versus the variance of the grey levels;
d) taking a pre-application digital image of a test subject of at least one of the following zones: middle zone of the brow, a zone of the cheek, an outer zone of the eye, and a zone of the nasogenian furrow;
e) measuring the variance of the grey levels over the set of pixels of the pre-application image;
f) calculating the pre-application apparent age of the test subject based on the calibration curve;
g) taking a post-application digital image of the test subject of the zone(s) imaged in step (d);
h) measuring the variance of the grey levels over the set of pixels of the post-application image;
i) calculating the post-application apparent age of the test subject based on the calibration curve;
j) assessing the anti-aging effect of the cosmetic product based on the difference between the pre-application apparent age and the post-application apparent age,
wherein the calibration curve takes into account the mean of at least the variance obtained from a plurality of images from a plurality of ageing zones of the face from a plurality of individuals.

29. The method of claim 1, wherein the calculating step further comprises calculating at least one of (i) the mean of the grey levels, and (ii) the surface area of the image over the set of pixels of the pre-application image.

* * * * *